US008481458B2

(12) United States Patent
Miles (10) Patent No.: US 8,481,458 B2
(45) Date of Patent: Jul. 9, 2013

(54) ADJUVANT FOR PESTICIDES

(75) Inventor: David Miles, Chapel Hill, NC (US)

(73) Assignee: CJB Industries, Valdosta, GA (US)

( * ) Notice: Subject to any disclaimer, the term of this patent is extended or adjusted under 35 U.S.C. 154(b) by 178 days.

(21) Appl. No.: 13/083,700

(22) Filed: Apr. 11, 2011

(65) Prior Publication Data

US 2011/0224081 A1  Sep. 15, 2011

Related U.S. Application Data

(63) Continuation of application No. 10/161,260, filed on May 31, 2002, now abandoned.

(51) Int. Cl.
*A01N 57/00* (2006.01)
*A01N 57/18* (2006.01)

(52) U.S. Cl.
USPC ............ 504/127; 504/128; 504/194; 504/208

(58) Field of Classification Search
None
See application file for complete search history.

(56) References Cited

U.S. PATENT DOCUMENTS

| | | | |
|---|---|---|---|
| 3,635,826 A | 1/1972 | Hamilton | |
| 3,836,669 A | 9/1974 | Dadeklan et al. | |

(Continued)

FOREIGN PATENT DOCUMENTS

| | | |
|---|---|---|
| CN | 1095412 | 11/1994 |
| CN | 1158694 | 9/1997 |

(Continued)

OTHER PUBLICATIONS

MSMA, Wikipedia encyclopedia, 2013.*

(Continued)

*Primary Examiner* — Alton Pryor
(74) *Attorney, Agent, or Firm* — Womble Carlyle Sandridge & Rice, LLP

(57) ABSTRACT

The invention relates to compositions useful in the field of agricultural chemistry and methods for making and using the compositions. The compositions include (i) a permeabilizing agent, and (ii) a active component, for example, a pesticide or plant growth regulator, and can include additional components as well, for example, flow agents. The permeabilizing agent, or a mixture of permeabilizing agents, acts as an adjuvant to the active component or chemicals to improve the degree of efficacy of the active component or speed of action of the active component. The permeabilizing agents are typically one or more chelating agents, cationic materials, anionic materials, and zwitterionic materials, and include polyphosphate salts. Examples of cationic materials include polyamines such as ethylenediamine and quaternary ammonium salts. The active components can be pesticides, herbicides, insecticides, fungicides, virucides, bacteriocides, and acaricides. Examples of suitable active components include plant growth regulators, defoliators, dessicants, transfection agents, wood treatments (CCA or other chemicals that are effective against termites), traps, disinfectants, marine paints and the like. The compositions can be prepared by mixing the components in a suitable manner, and the compositions can be used by applying the compositions to a plant in need of treatment thereof in an amount effective for the desired use, employing conventional application techniques. In one embodiment, the active components are defoliants, and the composition is used for plant defoliation, for example, with respect to cotton plants.

10 Claims, 1 Drawing Sheet metal complex metal chelate metal chelate

U.S. PATENT DOCUMENTS

| | | | |
|---|---|---|---|
| 3,880,613 A | | 4/1975 | Oswald et al. |
| 3,929,451 A | | 12/1975 | Cross et al. |
| 4,132,780 A | | 1/1979 | McConnell |
| 4,607,036 A | | 8/1986 | Borovian |
| 4,675,120 A | | 6/1987 | Martucci |
| 5,124,359 A | | 6/1992 | Wachman et al. |
| 5,180,587 A | | 1/1993 | Moore |
| 5,258,409 A | | 11/1993 | Gay |
| 5,312,558 A | | 5/1994 | West |
| 5,547,918 A | | 8/1996 | Newton et al. |
| 5,547,990 A | | 8/1996 | Hall et al. |
| 5,660,821 A | | 8/1997 | Birbara et al. |
| 5,661,111 A | * | 8/1997 | Kuramochi et al. ......... 504/284 |
| 5,723,406 A | | 3/1998 | Larose et al. |
| 5,728,649 A | | 3/1998 | Hasebe et al. |
| 5,853,785 A | | 12/1998 | Nayyar et al. |
| 5,863,909 A | | 1/1999 | Kurita et al. |
| 5,997,602 A | | 12/1999 | Aijala |
| 6,093,679 A | | 7/2000 | Azuma et al. |
| 6,149,913 A | | 11/2000 | Holmes |
| 6,200,586 B1 | | 3/2001 | Lambie et al. |
| 6,206,946 B1 | | 3/2001 | Hayashi et al. |
| 6,242,526 B1 | | 6/2001 | Siddiqui |
| 6,277,788 B1 | | 8/2001 | Wright |
| 6,352,585 B1 | | 3/2002 | Diesso |
| 6,440,440 B1 | | 8/2002 | Meerpoel et al. |
| 6,706,666 B2 | | 3/2004 | Hasebe et al. |
| 6,818,185 B1 | | 11/2004 | Chang et al. |
| 6,852,682 B2 | | 2/2005 | Small et al. |
| 6,897,185 B1 | * | 5/2005 | Chang et al. ............... 504/357 |
| 7,056,862 B2 | | 6/2006 | Hayashi et al. |
| 2003/0035847 A1 | | 2/2003 | Martucci |
| 2003/0176286 A1 | | 9/2003 | Gustavsson et al. |
| 2004/0071653 A1 | | 4/2004 | Bratescu et al. |
| 2004/0138176 A1 | | 7/2004 | Miles |
| 2004/0151749 A1 | | 8/2004 | Hasebe et al. |
| 2005/0002964 A1 | | 1/2005 | Bockmuhl et al. |

FOREIGN PATENT DOCUMENTS

| | | |
|---|---|---|
| FR | 2440601 | 5/1980 |
| JP | 56109281 | 8/1981 |
| JP | 06236001 | 8/1994 |
| PL | 161239 | 1/1991 |
| RO | 105352 | 8/1994 |

OTHER PUBLICATIONS

Russell, "Types of Antimicrobial Agents", Principles and Practice of Disinfection, Preservation and Sterilization, Ch. 2, pp. 21-27, 32-36, 55-56, 75-94, $3^{rd}$ Ed., Blackwell Publishing.

Merianos, "Surface-Active Agents", Disinfection, Sterilization and Preservation, Ch. 14, pp. 283-320, $5^{th}$ Ed., Lippincott Williams & Wiklins.

Database AUAB on West, Accession No. 1993-303856, Lisson et al, "Effervescent Toilet Deodorizers—uses liberated carbon di:oxide to carry active agent to air and water", AU 9332847, Aug. 12, 1993.

Database JPAB on West, Accession No. 1986-059770, "Bathroom liquid detergent composition contg. surfactant, hydroxyl polyvalent carboxylic acid and terpenic hydrocarbon solvent", JP61012789 A, Jan. 21, 1986.

Wei et al., Transport of Cadmium in Purple Soil Under Simulated Submerging Conditions and the Influencing Factors, Huanjing Kexue Xuebao, 2002, 22 (6), 696-700—ABS.

Dey et al., Efficacy and Radiation Stability of Some Decontaminant Formulations, Water Chemistry of Nuclear Reractor Systems, 1922, 6 (2), 312-313—ABS.

Lewis et al., "Seasonal Effects on Microbial Transformation Rates of an Herbicide in Freshwater Stream: Application of Laboratory Data to the Field Site,";1986; Environmental Toxicology and Chemistry; 5(9): 791-796.

Ramesh et al., "Interaction of Substerilizing Gamma Radiation and Thiodicarb Treatment for Management of the Tobacco Caterpillar *Spodopter litura*,"; 2002; Phytoparasitica; 30(1): 7-17.

\* cited by examiner

ADJUVANT FOR PESTICIDES

CROSS-REFERENCE TO RELATED APPLICATIONS

This application is a continuation of U.S. Ser. No. 10/161,260 filed May 31, 2002 now abandoned, the contents of which are incorporated herein by reference in its entirety.

FIELD OF THE INVENTION

The present invention relates generally to agricultural chemical compositions. Chemicals are used in connection with plants, lumber and trees. Such chemicals include insecticides, fungicides, herbicides, plant growth regulators, transfection agents, wood treatments, traps, disinfectants, house paints, marine paints and the like. Much research effort has focused on achieving the maximum effectiveness of these chemicals. However, it has been difficult to enhance the effectiveness of agricultural chemicals through adjustments in formulations, particularly when this results in lower concentrations or rates of application. For example, environmental regulations limit the amount of certain pesticides that can be applied to plants, and methods for lowering the effective amount of the pesticides are extremely beneficial. Therefore, further enhancement of existing agricultural chemicals would highly contribute to the industry.

Many crops that require mechanical harvesting need to have their leaves removed for the most efficient and economical production. Defoliation and desiccation are the two most common methods for removing mature leaves. During the growing season, leaves supply photosynthates and are shed only as a result of stress such as drought, disease, or cold. When the crop has matured, the leaves serve no beneficial purpose and can be removed to assist mechanical harvesting. Removing the large amount of foliage has become an important step in the harvesting of lucerne, potato and cotton crops, for example.

Chemical defoliation induces the loss of leaves before they would have normally been shed by the plant. This is the accepted agricultural practice, particularly with respect to cotton. Chemical defoliation is the process of inducing the plant to abscise its leaves through judicious injury. Abscission is a very complex biochemical process. Defoliant chemicals alter hormonal levels to achieve abscission, but their action is influenced by many environmental factors such as temperature, nutrient and moisture level as well as the maturity and hormonal balance within the plant. The major hormones that affect defoliation are the auxins, ethylene, abscisic acid, gibberellic acid, and cytokinin. Inorganic solutes and in particular calcium ions play a critical role in the transport and hence the action of the hormones. Many chemicals have been screened for their ability to defoliate cotton. There is still a need, however, for chemicals and chemical compositions and methods that, among other things, improve the degree or speed of defoliation, help control regrowth, or improve the speed or degree of the opening of mature bolls. It would be advantageous to have additional compositions and methods of improving the efficacy of agricultural chemicals. The present invention provides such compositions and methods.

SUMMARY OF THE INVENTION

In accordance with the purposes of this invention, as embodied and broadly described herein, this invention, in one aspect, relates to compositions for use in agricultural chemistry and methods of preparation and use thereof. The compositions include: (i) a permeabilizing agent, for example, a chelating agent, and (ii) an active component, particularly an active component useful for pest control or plant growth regulation.

The permeabilizing agent, for example, a chelating agent, a mixture of chelating agents, or a mixture of chelating agents and amines, acts as an adjuvant to the active component or chemicals to improve the degree of efficacy of the active component or speed of action of the active component. When in solid form, the compositions can also advantageously include a flow agent to avoid caking of the composition. Examples of suitable flow agents include HiSil and clays, such as Kaolin claims, for example, Polyfil DL. However, the compositions can also be used in liquid form.

Zwitterionic materials are one type of chelating agent. These include ethylene diamine tetraacetic acid and other compounds that include both amine and are carboxylic acid (and other acidic) functional groups. Other examples of suitable permeabilizing agents also include one or more cationic materials and anionic materials, and specifically include polyphosphates. Examples of cationic materials include polyamines such as ethylenediamine and quaternary ammonium salts. Examples of anionic materials include polycarboxylic acids such as oxalic acid, succinic acid, maleic acid, citric acid and the like. Another group of permeabilizers are agriculturally acceptable salts of all of these compounds.

Examples of suitable active components include plant growth regulators, defoliators, dessicants, transfection agents, wood treatments (CCA or other chemicals that are effective against termites and molds), traps, disinfectants, house paints, marine paints and the like. In one embodiment, the active components are nucleic acids that are used to transfect a plant. In one embodiment, the active components plant are defoliants, and the composition is used for plant defoliation, for example, with respect to cotton plants. In this embodiment, the chelating agent, or a mixture of chelating agents, acts as an adjuvant to the defoliant to improve the degree or speed of defoliation, help control regrowth, and/or improve the speed or degree of the opening of mature bolls of cotton. This type of composition can be used in a method for defoliating a plant, which method involves applying the composition to a plant substrate in an amount sufficient to effect defoliation.

In another embodiment, the active components are herbicides and their activity is improved by use of a permeabilizer by permitting more active ingredient to cross the cell wall. This allows lower use rates of the herbicide. Another embodiment is insecticides where the permeabilizer allows the insecticide to cross the insect cell wall; whether it be the insect cuticle for contact insecticides, or the insect gut for ingestion insecticides. In another embodiment the active ingredient is a fungicide. The permeabilizer allows the fungicide to penetrate the plant if it is a systemic fungicide, or to penetrate the fungus if it is a protectant fungicide. In another embodiment, the active ingredient is a bactericide. In this case the permeabilizer promotes the penetration of the bactericide into the bacteria before it can attack the plant.

In another embodiment, the active components improve the viability of plants to which they are applied, and are rendered more effective by their ability to cross the plant cell wall. In a further embodiment, the compositions are applied to lumber to help protect the lumber from spalting and other fungal infection, termite infestation, and the like. When applied to lumber in the context of marine applications, the treated lumber can be rendered more resistant to decay. Additional advantages of the invention will be set forth in part in the detailed description, which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory of preferred embodiments of the invention, and are not restrictive of the invention, as claimed.

DETAILED DESCRIPTION OF THE INVENTION

The present invention may be understood more readily by reference to the following detailed description of the invention. It is to be understood that this invention is not limited to the specific embodiments described, as specific embodiments may, of course, vary. It is also understood that the terminology used herein is used for the purpose of describing particular embodiments only and is not intended to be limiting. It must also be noted that, as used in the specification including the appended claims, the singular forms "a," "an," and "the" include plural references unless the context clearly dictates otherwise.

Ranges may be expressed herein as from about or approximately one particular value and/or to about or approximately another particular value. When such a range is expressed, another embodiment includes from the one particular value and/or to the other particular value. Similarly, when values are expressed as approximations, by use of the antecedent "about," it will be understood that the particular value forms another embodiment. A pesticide is defined by the Federal Government in 40 CFR 152.3 as "any substance (or group of structurally similar substances if specified by the Agency) that will prevent, destroy, repel, or mitigate any pest, or that functions as a plant regulator, desiccant or defoliant within the meaning of FIFRA sec. 2 (a)."

Agriculturally acceptable salts are those salts that do not adversely effect the activity of a desired compound or adjuvant.

An adjuvant is a chemical which assists the primary active ingredient to do its job better. This can be quicker action, lower use rates, or better results at the same rate. These include surfactants, and oils to improve wetting, some improve rainfastness. It has been stated recently that "a range of inorganic salts, phosphate esters, and chelating agents have been used to enhance herbicide activity; in many instances, however, data on the effects of these compounds on herbicide absorption are lacking, and there is no clear explanation of how these materials enhance herbicide activity." (Ref 6)

Adjuvants help, enhance or facilitate the effectiveness of another chemical or chemicals. They can be used with agricultural chemicals including, but not limited to herbicides, insecticides and fungicides. A cotton harvest adjuvant, for example, would be a chemical that improves the degree or speed of defoliation, helps to control regrowth, or improves the speed or degree of the opening of mature bolls provided by another chemical or mixture of chemicals. In essence, an adjuvant is a chemical that would improve the value of the harvested cotton crop when combined with other chemicals used for the above purposes.

In accordance with the present invention generally, it has been discovered that the class of chemicals known as permeabilizing agents, for example, chelators or complexing agents, cationics, anionics, zwitterionics, and combinations thereof, act as adjuvants with active components. In one embodiment, this invention comprises using a chelator or chelating agent and a active component in combination to effectuate plant defoliation. In other embodiments, the compositions are used to effectuate weed management, disease control and/or insect management.

Without being bound by any particular theory, it is believed that the addition of permeabilizing agents to the active components results in improved permeability through the plant cell wall, which results in improved efficacy of a large variety of agricultural chemicals, which are examples of the active components described herein. The permeabilizing agents interact at sites on the outer membrane surface, at which divalent cations crossbridge adjacent lipopolysaccharide molecules. This causes a destabilization of the outer membrane that permits uptake of the active component and/or other molecules in the cell environment. The permeabilizing agent promotes uptake by affecting the lipopolysaccharide or divalent cationic crossbridge and further assists with the molecular transport of the active component across membranes within the cell and from cell to cell.

I. Compositions

The compositions described herein include a permeabilizing agent and an active component. Permeabilizing agents and active components will be described in further detail below. The compositions or products described herein can be supplied as a solid or a liquid, including thixotropic droplets. The solid can be a granule or a powder. The liquid can be a solution, dispersion or suspension in water or other carrier. These products are generally diluted into water before being sprayed onto the field from either an airplane or ground application equipment. Solid formulations can be combined with wetting agents or surfactants for better deposition or application on the plants surface or substitute and better uptake by the plant. Solid formulations can be preferred because they offer higher loading levels.

A. Permeabilizing Agents

The permeabilizing agent functions by improving the permeability of the cell walls of the plant or plants to which it is applied. By improving the permeability of the cell walls, the active components have better penetration into the plant. Also, in the case of insects, bacteria, fungi, viruses and acaricides, the permeabilizing agents can improve the permeability of the cell walls of these agents and improve the passage of the active components into these biological entities, thus improving the efficacy of these compounds. Increased efficacy can translate into lower effective dosages, which is a tremendous benefit, particularly with governmental regulations constantly lowering the permitted dosages of these compounds. Further, as the active components penetrate the plant cell wall, they are more persistent than active components applied topically to plants that do not effectively penetrate the plant cell wall. Accordingly, an insect that attempts to ingest a plant, where the plant has an effective amount of an insecticide present inside the cell wall, may kill the insect long after conventional topically applied insecticides would be washed away.

One Class of Permeabilizers—Chelating Agents

Figure 1:
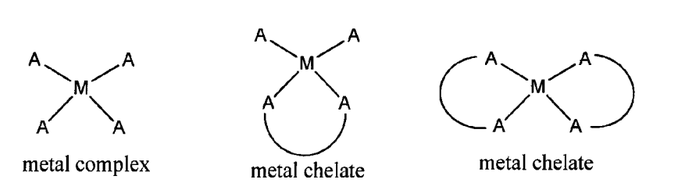
FIG. 1 illustrates a metal complex, a bidentate metal chelate, and a terdentate metal chelate.

A chelate, sometimes referred to as a sequestrant, a complex ion, and/or a coordination compound, is an organic compound that combines with a metal ion to form a complex in which the donor atoms are connected to each other as well as to the metal. Thus, the metal becomes part of a heterocyclic ring. (See FIG. 1). Donor atoms in the chelate complex may be tied together with additional chelate rings so that each chelating agent may contain two, three, four, five, six or even more donor groups. One of the best examples of this sort of chelate is EDTA, which has two amine donor groups and four carboxyl donor groups. It can thus supply the complete requirements for the coordination sphere of many metals with a single molecule where it might take three molecules of ethylenediamine to meet the same-requirements. A chelating agent that supplies two donor electrons to the metal is said to be bidentate. Similarly ter-, quadri, quinqui-, and sexadentate donors, bind the metal in 3, 4, 5, and 6 positions, respectively. Hence, EDTA is sexadentate and ethylenediamine is bidentate, for example.

Sometimes chelating agents combine with a metal ion to form soluble complexes that help the ions move across barriers. Examples of this are the use of humic acids by plants to dissolve trace elements and make them accessible. Other times chelating agents act to remove ions from solution or make transport more difficult. An example of the use of chelator for this purpose is the addition of EDTA, or its sodium salt, to hard water to keep emulsions from breaking.

In particular, chelating agents or mixtures of thereof added to active components in cotton improve defoliation, regrowth, and the opening of unopened bolls. Generally, chelating compounds that are useful for improving the activity of cotton active components include, but are not limited to sugars, amino acids, organic diacids, diamines, alpha ketoacids, alphahydroxyacids, aminodiacids, amino triacids, amino tetraacids, tdol amines, and organic polyacids and their sodium, potassium, and ammonium salts. Specific examples of these chelating compounds include, but are not limited to the sugars, acids and salts of maleic acid, malonic acid, tartaric acid, citric acid, glycine, lactic acid, malic acid, succinic acid, oxalic acid, dextrose, ethylenediaminetetraacetic acid (EDTA), tris(hydroxymethyl)aminomethane, lactose, mannitol, glutaric acid, malic acid, succinic acid, glycerol, humic acid, fulvic acid, sorbic acid, sorbose, ethylene diamine, 1,2 diaminocyclohexane, trimethylenediamine, tetramethylenediamine, 1,2 diaminopropane, diethylenetriamine, triethylenetetramine, triaminodiethylamine, N-hydroxyethylethylenediamine, sodium polyphosphate, potassium polyphophate, ammonium polyphosphate, sodium hexametaphosphate and mixtures thereof. The chelating agent used in the present compositions can be 100% of any particular chelator, or a combination of chelator in any ratio. A combination or mixture of chelating compounds may dissolve faster than a single compound. However, 100% oxalic acid, 100% citric acid, 100% EDTA, and combinations of these three are preferred.

Chelating agents are believed to function by sequestering divalent metal ions and keeping them from ordering the lipopolysaccharide layer in the plant cell walls. The voids may then be filled with phospholipids which are much more permeable. The activity of some chelating agents is enhanced by amines and other cationic substances, such as tris, ethylamine, propylamine, diethanolamine, and 3-aminopropanol. Cationics are described in more detail below.

Cationics

The permeabilizing agent can be any cationic compound capable of permeabilizing the plant cell wall. Cationic compounds, for example, polycationic compounds and cationic surfactants, alter the ordering of the lipopolysaccharide layer in plant cell walls by replacing the divalent cationic bridging metal ions. The negatively charged lipopolysaccharide layer which normally binds to the positively charged metals binds to the much bulkier cationic amines creating gaps in the lipopolysaccharide layer.

In one embodiment, the cationic compound is a polycationic compound, for example, a polyamine such as (diethylenetriamine, triethylenetetramine, tetraethylenepentamine, polyethylene polyamine N-oleylamine polyhexamethamine polyamine, and the like).

Quaternaty ammonium salts can be preferred, and cocodimethyl and dicocodimethylammonium chloride are even more preferred, as are other coco-substituted quaternary ammonium salts.

Examples of tertiary amines that can be used include tertiary amines including linear alkyl groups or a linear alkenyl groups with a carbon number of 8 to 20, and can be derived from natural oil or fat, and can also include one or more an oxyalkylene groups. Preferred tertiary amine include mono-long-chain alkylamine, for example, bis(2-hydroxyethyl)cocoamine, bis(2-hydroxyethyl)-tallowamine, bis(2-hydroxyethyl)oleylamine, and bis(2-hydroxyethyl)laurylamine. Further, included are polyoxyalkylenated long-chain alkylamine, for example, bis(polyoxyethylene (EOp=3 to 30)) cocoamine, bis(polyoxyethylene (EOp=3 to 30))tallowamine, bis(polyoxyethylene (EOp 3 to 30))oleylamine, bis (polyoxyethylene (EOp=3 to 30))laurylamine, bis (polyoxyethylene (EOp=3 to 30))palmstearylamine, bis (polyoxyethylene (EOp=3 to 10)polyoxypropylene-(POp=3 to 10)cocoamine, and bis(polyoxyethylene (EOp=3 to 10) polyoxypropylene (POp=3 to 10)tallowamine. In the compounds described above, EOp represents an average addition mole number of ethylene oxide, and POp represents an average addition mole number of propylene oxide.

Derivatives derived from these tertiary amines can be used as well. Examples of these derivatives include amine salts, quaternized products, betaines, and amine oxides. The tertiary amine salts include salts of inorganic acids such as hydrochloric acid and sulfuric acid, and salts of organic acids such as acetic acid. In particular, hydrochlorides and acetates are preferred. The quaternized products of the tertiary amines described above can be obtained by using known quaternizing agents. The quaternizing agents include dialkylsulfuric acids (an alkyl group having a carbon number of 1 to 3) and halogenated alkyl (an alkyl group having a carbon number of 1 to 3, a benzyl group).

The quaternary salts are advantageously methyl chloride-quaternized products, benzyl chloride-quaternized products, dimethylsulfuric acid-quaternized products and diethylsulfuric acid quaternized products of the tertiary amines described above.

Further, the following quaternary ammonium salts are preferred as well:
(A) quaternized long-chain amines
　(a) tri-lower alkyl long-chain alkylammonium chloride
　　(i) trimethylcocoammonium (coco=$C_{12}$ to $C_{15}$ alkyl) chloride
　　(ii) trimethyloctadecylammonium chloride
　(b) dialkyldi-lower alkylammonium chloride
　　(i) dimethyldioctadecylammonium chloride
　　(ii) dimethyldicocoalkylammonium chloride
(B) quaternized polyoxyalkylenated long-chain amines
　(a) alkyldi(polyoxyethylene) lower alkylammonium chloride
　　(i) methylbis(omegahydroxypoly(oxyethylene)-oleo)ammonium chloride in which polyoxyethylene is derived from 2 to 30 moles of ethylene oxides.

The following products are suitable as amine oxides derived from the tertiary amines:
(A) trialkylamine oxide
　(i) lauryldimethylamine oxide
　(ii) stearyldimethylamine oxide (B) dihydroxyethylalkylamine oxide
 (i) dihydroxyethyloctylamine oxide
 (ii) dihydroxyethyldodecylamine oxide
 (iii) dihydroxyethyltallowlamine oxide
(C) di(polyoxyethylene)alkylamine oxide
 (i) bis(polyoxyethylene)tallowamine oxide
 (ii) bis(polyoxyethylene)cocoamine oxide
 (iii) bis(polyoxyethylene)dodecylamine oxide
(D) lower alkylpolyoxyethylenealkylamine oxide
 (i) methylpolyoxyethylenecocoamine oxide.

The amines or derivatives thereof are typically blended into the composition in a proportion of 10 to 30 weight %, preferably 15 to 25 weight %.

Anionics

The permeabilizing agent can further be any anionic compound capable of permeabilizing the plant cell wall. In one embodiment, the anionic compound is an anionic surfactant or a polyanionic compound, for example, a polymer such as a polyacid such as polylactic acid, polyphosphates and polyacrylates, or monomers such as citric acid EDTA and others listed above. Other anionics which remove calcium would be sulfate ion which would form insoluble calcium sulfate. Usable forms of sulfate ion would be ammonium sulfate, sodium sulfate, potassium sulfate, hydrogen sulfate or any mixture thereof.

Zwitterionics

Zwitterionic compounds can also be preferred chelating agents. Zwitterionic compounds are those that include both a positive and a negative charge on the same molecule. Examples include amino acids and polyamine polycarboxylic acids. Many of the above-mentioned chelating agents are zwitterionic.

Betaines derived from the tertiary amines include trialkylbetaines, including long-chain alkyldi-lower alkylbetaines such as lauryldimethylbetaine, stearyldimethylbetaine, cocodimethylbetaine, and decyldimethylbetaine.

Salts

Calcium and magnesium salts can also serve as permeabilizers. They function in the opposite way from chelators or amines in that they provide too much rigidity to a cell wall and it becomes brittle and hence more permeable. Soluble salts such as calcium and magnesium chlorides, nitrates, sulfites, thiosulfates, nitrite, bisulfites, or salts of organic compounds such as calcium or magenesium lactate, citrate, etc.

Combinations

Combinations of chelating agents and cationic compounds can be preferred. Combinations of oxalic acid and citric acid are particularly preferred, as oxalic acid is a good permeabilizer but exhibits some toxicity on exposure, for example, producing kidney stones. Citric acid lowers oxalic acid toxicity and also functions as a permeabilizer. Combinations of chelators and quaternary ammonium salts are also particularly preferred.

Solvents

In some embodiments, the permeabilizers and, optionally, active components, are provided in an aqueous solution. However, other water-miscible solvents can also be used, typically in concentrations of less than 25% by volume. These solvents include, but are not limited to, $C_{1-5}$ alcohols such as ethanol, propanol and isopropyl alcohol, polyhydric alcohols such as glycerol, pentaerythritol, and the like, dimethyl sulfoxide, dimethyl formamide, glymes, acetone and the like. Crop oils can also be used.

B. Active Components

Any type of agricultural chemical, pesticide or genetic material, which results in a desired effect on a plant can be used. The active components can be herbicidal, pesticidal, insecticidal, bactericidal, virucidal, fungicidal, acaricidal, and the like. The active components can be genetic material to be transfected into a plant.

Pesticides

A pesticide is defined by the Federal Government in 40 CFR 152.3 as "any substance (or group of structurally similar substances if specified by the Agency) that will prevent, destroy, repel, or mitigate any pest, or that functions as a plant regulator, desiccant or defoliant within wording the meaning of FIFRA sec. 2 (a)." Several types of pesticides are described in more detail below.

Plant Growth Regulators

Any compound that regulates plant growth can be included in the compositions of the invention. Examples of the plant-growth regulator include defoliators and desiccants. Specific examples include MH (maleic hydrazide), ethephon (2-chloroethylphosphonic acid), Folex (S,S,S, tributyl phosphorothioate, Dropp (thidiazuron), Pix (mepiquat chloride). Any defoliating compound that is effective at defoliating a desired plant can be used. Examples of suitable defoliating agents include paraquat, diquat, endothall, chlorates, ethephon, tributylyphosphorthoate, cacodylic acid and its sodium salt, MSMA, diuron, dimethipin, monocarbamide, carfentrazone, cyclanalide and thidiazuron.

Formulations of magnesium and sodium chlorate were among the first products to experience widespread use. Organophosphates, such as tributyl phosphorothioate, were found to defoliate cotton without excessive drying. Cacodylic acid was found effective in the western United States where there are differences in the cotton plants. Two of the more recently developed defoliant chemicals are dimethipin and thidiazuron. They are as effective as the chlorates or phosphates at defoliation, but are superior for regrowth control. The plant hormone ethylene, usually supplied to the plant in the form of 2-chloroethylphosphonic acid, is used to open immature cotton bolls and increase yield, but can cause defoliation, although it is not usually sufficient by itself for commercial levels of defoliation. Recently, a combination product of 2-chloroethylphosphonic acid and cyclanilide (FINISH®) was found to provide commercially acceptable defoliation. Many times, combinations of the above-mentioned chemicals are used to achieve the desired level of defoliation, regrowth control and boll opening under the existing environmental conditions. These are all considered active components.

It is believed that, in addition to the benefit of increased permeation, the chelation of calcium ions has a beneficial effect on auxins. As mentioned above, defoliation and boll opening are the result of many plant hormones, two of the most noticeable being ethylene and the auxins. These two hormones have opposing effects on the plant for many processes. Ethylene causes ripening, abscission, and. senescence. Auxin inhibits these processes. However, auxin requires calcium ions for efficient transport. It is well recognized that inorganic solutes, and specifically calcium, can affect the action of hormones and exogenous growth regulators. The application of chelators, specifically calcium chelators, can slow the transport of auxin and enhance the action of exogenous active components.

The chelating agent application rate used in the defoliation method ranges from about 0.1 pound per acre to about 5 pounds per acre, preferably from about 0.25 to about 2.5 pounds per acre. The chelating agents can be used and/or applied with paraquat, diquat, endothall, chlorates, ethephon, tributylyphosphorothioate, cacodylic acid and its sodium salt, MSMA, diuron, dimethipin, monocarbamide, carfentrazone, cyclanalide and thidiazuron in ratios from 1:100 to 100:1, preferably from 1:10 to 10:1.

Herbicides

Any herbicide that causes the desired result can be used. Herbicides are generally broken down into broad categories, including pre-plant herbicides, burndown herbicides, and post-emergence herbicides. Those of skill in the art of farming know when it is appropriate to use a particular type of herbicide.

There are several classes of post-emergent herbicides. These include:
A. Downwardly Mobile Herbicides [Symplastically Translocated (leaf to growing points)]
  1. Auxin Growth Regulators
    Phenoxy
    Benzoic acid derivatives
    Picolinic acid derivatives
  2. Amino Acid Inhibitors (aromatic)
    Glyphosate
    Sulfosate
  3. Amino acid inhibitors
    Sulfonyl Ureas
    Imidazolinones
    Sulfonanalides
  4. Pigment Inhibitors
  5. Grass Meristem Destroyers (Lipid Biosynthesis Inhibitors)
    Aryloxyphenoxypropionates
    Cyclohexanediones
B. Non Translocated (Contact Herbicides)
  1. Cell Membrane Destroyers
    Bipyridyliums
    Diphenyl ethers (nitrophenyl ethers)
C. Upwardly Mobile Only Herbicides (Apoplastically Translocated)
  1. Photosynthetic Inhibitors
    Triazines
    Uracils
    Phenylureas
    Nitriles Examples of acid amide-based herbicides include Stam (3',4'-dichloropropionanilide, DCPA) and Alachlor (2-chloro-2',6'-diethyl-N-(methoxymethyl)-acetanilide). Examples of urea-based herbicides include DCMU (3-(3,4-dichlorophenyl)-1,1-dimethylurea) and Rinuron (3-(3,4-dichlorophenyl)-1-methoxy-1-methylurea). Examples of sulfonyl urea-based herbicides include thifensulfuronmethyl (methyl-3-(4-methoxy-6-methyl-1,3,5-triazin-2-ylcarbamoylsulfamoyl)-2-tanoate) and Flazesulfuron (1-(4,6-dimethoxy pyrimidin-2-y1)-3-(3-trifluoromethyl-2-pyridylsulfonyl)urea). Examples of dipyridyl-based herbicides include Paraquat dichloride (1,1'-dimethyl-4,4'-bipyridinium dichloride) and Diquat dibromide (6,7-dihydrodipyride[1,2-a:2',1'c]-pyrazinediium dibromide). Example of diazine-based herbicides include Bromacil (5-bromo-3-sec-butyl-6-methyluracil). Examples of S-triazine-based herbicides include Gesatop (2-chloro-4,6-bis(ethylamino)-1,3,5-triazine) and Simetryn (2,4-bis(ethylamino)-6-methylthio-1,3,5-triazine). An example of nitrile-based herbicides include DBN (2,6-dichlorobenzonitrile). Examples of dinitroaniline-based herbicides include Trifluralin (alpha,alpha,alpha-trifluoro-2,6-dinitro-N,N-dipropyl-p-toluidine). Examples of carbamate-based herbicides include Thiobencarb (Saturn) (S-p-chlorobenzyl diethylthiocarbamate) and MCC (methyl-3,4-dichlorocarbenzylate. NIP (2,4-dichlorophenyl-p-nitro-phenyl ether) is an example of diphenyl ether-based herbicides. PCP (sodium pentachlorophenoxide) is an example of a phenol-based herbicide. MDBA (3,6-dichloro-2-methoxybenzoic acid dimethylamine salt) is an example of a benzoic acid-based herbicide. Examples of phenoxy-based herbicides include 2,4-D sodium salt (sodium 2,4-dichlorophenoxyacetate), 2,4 D Esters, and Mapica ([4-chloro-o-toluoyl)oxy]aceto-o-chloroanilide. Examples of organic phosphorus-based herbicides include Glyphosate (N-(phosphonomethyl)glycinate, Bialaphos (sodium salt of L-2-amino-4-[(hydroxy(methyl)phosphinoyl]-butylyl-alanyl-N-alanine), and Glufosinate (ammonium DL-homoalanin-4-yl(methyl)phosphinate). TCA sodium salt (sodium trichloronate) is an example of an aliphatic group-based herbicides. Hydrogen peroxide is another herbicide.

Among these herbicides, the dipyridyl-based herbicides and the organic phosphorus-based herbicides are preferred. Among them, the organic phosphorus-based herbicides are more preferred, and Bialaphos (sodium salt of L-2-amino-4-[hydroxy)(methyl)phosphinoyl]-butyl-L-alanyl-N-alanine), Glufosinate (ammonium DL-homoalanin-4-yl(methyl)phosphinate), or Glyphosate (N-(phosphonomethyl)glycinate) are particularly preferred.

Insecticides

Any insecticide that is effective against a particular insect to be eliminated from a particular crop or site can be used. Examples of pyrethroid type insecticides include Fenvalerate (alpha-cyano-3-phenoxybenzyl-2-(4-chlorophenyl)-3-methylbutanoate) and Baythroid (cyano-4-fluoro-3-phenoxybenzyl-3-(2,2-dichlorovinyl)-2,2-dimethylcyclopropanecarboxylate). Organic phosphorus type insecticides include DDVP (2,2-dichlorovinyldimethyl phosphate), Sumithion (MEP) (dimethyl 4-nitro-m-tolyl phosphorothioate), Malathion (S-1,2-bis(ethoxycarbonyl)ethyldimethyl phosphorodethioate), Dimethoate (dimethyl S—(N-methylcarbamoyl methyl) phosphorodithioate), Elsan (S-[alpha-(ethoxycarbonyl)benzyl]dimethyl phosphorodithioate), and Baycid (dimethyl 4-methylthio-m-tolyl phosphorothioate). Carbamate type insecticides include Bassa (O-sec-butylphenyl methylcarbamate), MTMC (m-tolylmethylcarbamate), Meopal (3,4-dimethylphenyl-N-methylcarbamate), and NAC (1-naphthyl methylcarbamate), and Methomyl (S-methyl-N-(methylcarbamoyloxy)thioacetimidate), and Cartap (SS'-2-dimethylamino trimethylene bis-(thiocarbamate)), for example. Natural insecticides include pyrethrin preparations and piperonyl butoxide preparations which originate from Chrysanthemum cinerariaefolium, rotenone preparations, which originate from Derris which is a shrub of the pulse family, and nicotine (3-(1-methyl-2-pyrrolidinyl)pyridine sulfate) preparations originating in derris shrubs of Family Legumoinosae. Examples of the insect growth regulators (IGR), Diflubenzuron (1-(4-chlorophenyl)-3-(2,6-difluorobenzoyl)urea), Teflubenzuron (1-[3,5-dichloro-2,4-difluorophenyl)-3-(2,6-difluorobenzoyl)urea), Chlorfluazuron (1-[3,5-dichloro-4-(3-chloro-5-trifluoromethyl-2-pyridiloxyphenyl]-3(2,6-difluorobenzoyl)urea, Buprofezin (2-tert butylimino-3-isopropyl-5-phenyl-3,4,5,6-tetrahydro-2H-1,3,5-thiadiazin-4-one), and Fenoxycarb (ethyl 2-(4-phenoxyphenoxy)ethylcarbamate). Bactericides, Fungicides and Virucides Any bactericide, fungicide or virucide that is effective at a particular bacteria, fungus or virus can be incorporated into the compositions described herein and applied to a desired crop or situs. Examples of suitable bactericide and fungicides include Dithane (zinc ethylenebis(dithiocarbamate)), Maneb (manganese ethylenebis(dithiocarbamate)), Thiram (bis(dimethylthiocarbamoyl)disulfide) Manzeb (complex of zinc and manganese ethylenebis(dithiocarbamate), Bisdithane (bisdimethyl dithiocarbamoyl zinc ethylene bisdithiacarbamate), and Propineb (polymeric zinc propylenebis(dithiocarbamate), benzimidazole-based bactericides including Benomyl (methyl 1-(butylcarbamoyl)-2-benzimidazole carbamate) and Thiophanate-methyl (dimethyl(4,4'-o-phenylenebis(3-thioallophanate)), and Vinclozolin (3-(3,5-dichlorophenyl)-5-methyl-5-vinyl-1,3-oxazolidine-2,4-dione), Iprodione (3-(3,5-dichlorophenyl)-N-isopropyl-2,4-dioxoimidazolidine-1-carboxamide), Procymidone (N-(3,5-dichlorophenyl)-1,2-dimethylcyclopropane-1,2-dicarboximide), Anilazine (2,4-dichloro-6-(o-chloroanilino)-1,3,5-triazine), Triflumizole ((E)-4-chloro-.alpha.,.alpha.,.alpha.-trifluoro-N-(1-imidazol-1-yl-2-propoxyethylidene)-toluidine), Metalaxyl (methyl-N-(2-methoxyacetyl)-N-(2,6-xylyl)-DIL-alaninate), Bitertanol (all-rac-1-(biphenyl-4-yloxy)-3,3-dimethyl-1-(1,2,4-triazol-1-yl)butan-2-o 1), Pyrifenox (2',4'-dichloro-2-(3-pyridyl)acetophenone-(EZ)—O-methyloxime), Fenarimol (2,4'-dichloro-.alpha.-(pyrimidin-5y1)benzhydrylalcohol), Triforine (1,4-bis-(2,2,2-trichloro-1-formamidoethyl)-piperazine), Guazatine iminoctadine (1,1-iminiodi(octamethylene)diguanidinium triacetate), Oxine-copper, antibiotic bactericides (streptomycin type, tetracycline type, polyoxins type, blasticidin S type, kasugamycin type, and validamycin type), Triadimefon (1-(4-chlorophenoxy)-3,3-dimethyl-1-(1,2,4-triazol-1-yl)-2-butanone), Isoprothiolane (diisopropyl-1,3-dithiolan-2-ylidenemalanate), Daconil (tetrachloroisophthalonitrile), Pansoil (5-ethoxy-3-trichloromethyl-1,2,4-thiadiazole), Fthalide (4,5,6,7-tetrachlorophmalide), Kitazin-P (0,0-diisopropyl-phosphorothioate), Hinosan (ethyl S,S-diphenylphosphorodithioate), Probenazole (3-allyloxy-1,2-benzisothiazol 1,1-dioxide), Captan (N-(trichloromethylthio)-4-cyclohexene-1,2-dicarboximide), Fosetyl (aluminum tris(ethylphosphonate)), and quaternary ammonium compounds.

Acaricides

Any suitable acaracide can be used. Examples of suitable acaricides include Sumiito (2-tert-butyl-5-(4-tert-butylbenzylthio)-4-chloropyridazine-3-(2H)-one), Acricid (2,4-dinitro-6-sec.-butylphenyldimethylacrylate), Chloromite (isopropyl 4,4-dichlorobenzylate), Akar (ethyl 4,4'-dichlorobenzilate), Kelthane (2,2,2-trichloro-1,1-bis(p-chlorophenyl)ethanol), Citrazon (benzoic 3-chloro-N-ethoxy-2,6-dimethoxybenzimidic anhydride), Omite (2-(p-tert-butylphenoxy)cyclohexyl propyn-2-yl sulfite), Osadan (bis[tris(2-methyl-2-phenylpropyl)tin]oxide), Hexythiazox (trans-5-(4-chlorophenyl)-N-cyclohexyl-4-methyl-2-oxothiazolidine-3-carboxamide), and Amitraz (N,N-bis(2,4-xylyliminomethyl)methylamine).

Transfection Agents

There are numerous known transfection agents, any of which can be used in the compositions described herein. The transfection agents are used in combination with genetic material to be transfected into a cell, and optionally, an appropriate vector, for example, an adenoviral vector. The genetic material can be any genetic material capable of effecting a desired alteration in the plant genetic code, and can be in the form of a plasmid. The genetic material is preferably DNA.

Wood Treatment Chemicals

Any wood treatment chemical capable of inhibiting destruction of wood by termites, fungus, mold and the like can be used. Examples of suitable wood treatment chemicals include CCA, polyethylene glycol, fungicides, termiticides, and known fungicides.

Traps

Traps are well known in the art for controlling insect populations. They typically include a chemical that attracts a desired insect, for example, a pheremone or other insect attractant, and also typically include an insecticide. Traps are well known for use in controlling populations of burrowing insects, flying insects or crawling insects, for example, roaches, ants, Japanese beetles, termites, mosquitoes and many other insects. The traps as described herein further include a permeabilizer to enhance the ability of the insecticide to control the insects.

Disinfectants/Antibacterial Agents

Any suitable disinfectant/antibacterial agent can be used. Examples of suitable disinfectants/antibacterial agents include the following:

| | |
|---|---|
| Quaternary ammonium salts | Captan |
| Alcohols | Essential oils |
| Organic acids | Triazines |
| Phenols | Iodine |
| Halo and Nitro phenols | Isothiozolones |
| Terpenes | Acridines |
| Esters of para-hydroxybenzoic acid | Aldehydes |
| Aromatic diamidines | Biguanidines |
| Anionic Surfactants | Nonionic surfactants |
| Betaines | Quinones |
| Quinolines | Hydrogen Peroxide |
| Peracetic acid | Heavy metal derivatives |
| Derivatives of 1,3 dioxane | Derivatives of imidazole |
| Derivatives of hexamine | |

Marine and House Paints

Suitable marine and house paints are well known to those of skill in the art. In one particular embodiment, the paint formulation includes the permeabilizing agents and also includes wood preservation chemicals, thereby further stabilizing the wood. House paints typically include an aqueous solvent and a latex material.

Optional Components

Additional optional components that can be present in the composition include adjuvants currently used with agricultural chemicals, such as flow agents, buffering agents, antifoam agents, compatibility agents, crop oil concentrates, deposition agents, dispersants, drift control agents, penetrants, surfactants, spreaders, and wetting agents.

Flow Agents

Any flow agent that is able to minimize or avoid caking of the composition can be used, typically in amounts of between 0.1% and 10%. Examples of suitable flow agents include silica gels; both fumed and precipitated and clays such as kaolin, talc, diatomaceous earth.

II. Methods of Making the Compositions

The compositions can be prepared in solid form by mixing the components, for example, using a blender, fitzmill or other suitable apparatus. Optionally, but preferably, the solid formulations include a flow agent. The flow agent is advantageously added to the solid components in a suitable amount to promote even flow of the material.

The compositions can also be prepared in liquid form, by adding the components to a desired solvent or dispersant. The dispersant can be, for example, a crop oil, water, or an aqueous solution including water soluble organic solvents such as ethanol. They can also be prepared as dispersions in a liquid either singly or as combinations with other suspensions or solutions of other permeabilizers.

The compositions are typically prepared with the active ingredients listed above present in a concentration in the formulated product at a level well above what is needed to make a good formulation, where the permeabilizers are incorporated to function as dispersants, wetting agents, emulsifiers, water softeners and the like. The permeabilizers are present at levels that affect the activity of the active ingredient by increasing the permeability across the plant cell wall. That is, at relatively low concentrations, for example, less than 5% by weight, more typically, between 0.5 and 3.0 percent by weight, the permeabilizers function by bringing aqueous and non-aqueous phases together. However, at relatively higher concentrations, i.e., greater than 5% by weight, more preferably greater than 10% by weight, the compounds not only bring aqueous and non-aqueous phases together, but also enhance the ability of the active compounds to cross plant cell walls.

III. Methods of Using the Compositions

The compositions are generally applied to a plant in need of treatment thereof in an effective amount to effect such treatment. The compositions can be applied by conventional application techniques. These techniques include, but are not limited to, root application, leaf application, crop dusting, spray application, and the like. They can also be used with coatings; for example wood treatment, paint, or other surface treatments.

Plant Growth Regulation

In one embodiment, the compositions are used to defoliate a plant. In this embodiment, an effective, defoliating amount of a composition including a permeabilizing agent, and a defoliator is applied to a plant surface. In one embodiment, the permeabilizing agent is a mixture of citric acid and oxalic acid. The composition can further includes a flow agent such as silica or kaolin clay.

Transfection

In another embodiment, the compositions are used to transfect a plant cell. In this embodiment, the composition includes a permeabilizing agent and a nucleic acid suitable for effecting the desired transfection.

Pest Control

In another embodiment, the compositions are used to treat a plant with a pesticide, herbicide, insecticide, fungicide, virucide, bacteriocide, and for acaricide. The methods involve applying to the plant an effective pesticidal, herbicidal, insecticidal, fungicidal, virucidal, bacteriocidal, and/or acaricidal amount of a composition including a permeabilizing agent and a pesticide, herbicide, insecticide, fungicide, virucide, bacteriocide, and/or acaricide.

Weed Control

The formulations described herein can also be used to enhance the results obtained with conventional weed control formulations. Weed control essentially involves applying a compound that selectively controls one type of plant in the presence of another. Examples include crabgrass-selective compounds that have little or no effect on grass. Weed control agents can be combined with the permeabilizing agents described herein to form enhanced weed control agents, enhanced due to their ability to permeate through the cell walls of the undesired weeds. In all of these embodiments, the chelating agents are typically the sugars, acids and salts of maleic acid, malonic acid, tartaric acid, citric acid, glycine, lactic acid, malic acid, succinic acid, oxalic acid, dextrose, ethylenediaminetetraacetic acid (EDTA), tris(hydroxymethyl)aminomethane, lactose, mannitol, glutaric acid, malic acid, succinic acid, glycerol, humic acid, fulvic acid, sorbic acid, sorbose, ethylene diamine, 1,2 diaminocyclohexane, trimethylenediamine, tetramethylenediamine, 1,2 diaminopropane, diethylenetriamine, triethylenetetramine, triaminodiethylamine, N-hydroxyethylethylenediamine, some quaternary ammonium salts, dimethyl amines, and agriculturally acceptable salts thereof, and mixtures thereof.

EXAMPLES

In most of the examples below, use rates lower than generally recommended were used to insure less than 100% kill. Some unrecognized compounds are also used for comparison. The Adjuvant 1 formulation is 77 percent by weight oxalic acid, 20 percent by weight citric acid and 3 percent by weight HiSil 233. Adjuvant 2 was 99.8 percent by weight oxalic acid, and while its efficacy is shown below in the examples, may be less preferred than Adjuvant 1 due to relatively poor flow and caking properties. Adjuvant 3 was a commercially supplied aqueous solution of EDTA tetra sodium salt solution. Adjuvant 4 was 99% citric acid. Adjuvant 5 was a mixture of 77 percent oxalic acid, 20% citric acid and 3 percent Polyfil DL. Adjuvant 6 (in Water) included 20 percent EDTA salt, 5 percent dicocodimethylammonium chloride, 1 percent cocodimethylamine, and 7 percent propylene glycol.

Example 1

Effectiveness of Dicamba Herbicide on Canada Thistle

This test was used to determine the effectiveness of dicamba herbicide on the weed Canada Thistle. The dicamba was mixed with water in a spray tank at the listed rate alone (A) or with a permeabilizer (B) and the degree of control of the weed was evaluated. Dicamba alone had an efficiency of about 13% and only slightly damaged the plant leaves. The dicamba and adjuvant mixture had an efficiency of about 62% and caused was major damage to leaves and stems of the plant. The ratings were made at 2 days. A week later plants treated with dicamba alone had nearly recovered while plants treated with dicamba and adjuvant 1 were nearly dead.

A. Dicamba dimethylamine salt—1 oz/gal
B. Dicamba dimethlyamine salt—1 oz/gal+Adjuvant 1 40 g/gal
Herbicidal Efficiency—2 day rating
Weed Thistle
A. 13%
B. 62%

Example 2

Effectiveness of Fluazifop-Butyl on Fescue Grass This test was used to determine the effectiveness of fluazifop-butyl herbicide on fescue grass. The herbicide was mixed with water in a spray tank at the listed rate with only a nonionic surfactant (NIS) treatment (A) or with a NIS and a permeabilizer (B) and the degree of control of the grass was evaluated. The effectiveness of fluazifop alone was about 3%, and resulted in only slightly damaged leaves. The fluazifop combined with the permeabilizer had an effectiveness of about 42%, resulting in major damage to leaves and stem. The ratings were made at 4 days. A week later fescue treated with fluazifop alone had nearly recovered while fescue treated with fluazifop combined with the permeabilizer was nearly dead.

A. Fluazifop-Butyl—1.25 oz/gal+NIS ⅙ Tsp/gal
B. Fluazifop-Butyl—1.25 oz/gal+NIS ⅙ Tsp/gal+EDTA 6 oz/gal
Herbicidal Efficiency—4 Day Evaluation
Weed Fescue Grass
A. 3%
B. 42%

Example 3

Effectiveness of Hydrogen Peroxide as a Herbicide

In this example, hydrogen peroxide was used as a screen for permeabilizing agents because hydrogen peroxide by itself it is not a very efficient herbicide. As shown below, the 
effectiveness of hydrogen peroxide was potentiated by permeabilizers that help it cross the outer membrane. A number of mixtures of permeabilizers were identified. The hydrogen peroxide was mixed into water at the given rate with nonionic surfactant (NIS) and various permeabilizers to form compositions A through W. These compositions were sprayed on clover for evaluation. The degree of damage to the clover was assessed.

A. 50% Hydrogen Peroxide 6 oz/gal+1/6 Tsp NIS/gal
B. 50% Hydrogen Peroxide 6 oz/gal+1/6 Tsp NIS/gal+EDTA 6 oz/gal
C. 50% Hydrogen Peroxide 6 oz/gal+1/6 Tsp NIS/gal+EDTA 6 oz/gal+Tris 3 oz/gal
D. 50% Hydrogen Peroxide 6 oz/gal+1/6 Tsp NIS/gal+Dimethyldicocoammonium chloride 1.5 oz/gal
E. 50% Hydrogen Peroxide 6 oz/gal+1/6 Tsp NIS/gal+Oxalic Acid 4 oz/gal
F. 50% Hydrogen Peroxide 6 oz/gal+1/6 Tsp NIS/gal+Adjuvant 1 4 oz per gallon
G. 50% Hydrogen Peroxide 6 oz/gal+1/6 Tsp NIS/gal+Adjuvant 1 4 oz/gal+Dicocodimethylammonium chloride 0.5 oz/gal
H. 50% Hydrogen Peroxide 6 oz/gal+1/6 Tsp NIS/gal+Adjuvant 1 4 oz/gal+Dicocodimethylammonium chloride 0.5 oz/gal+KOH 4 oz/gal
I. 50% Hydrogen Peroxide 6 oz/gal+1/6 Tsp NIS/gal+Adjuvant 1 4 oz/gal+Dicocodimethylammonium chloride 0.5 oz/gal+NH4OH 2 oz/gal
J. 50% Hydrogen Peroxide 6 oz/gal+1/6 Tsp NIS/gal+Citric Acid 4 oz/gal
K. 50% Hydrogen Peroxide 6 oz/gal+1/6 Tsp NIS/gal+Citric Acid 4 oz/gal+KOH 3 oz/gal+Dicocodimethylammonium chloride 2C75 0.5 oz/gallon
L. 50% Hydrogen Peroxide 6 oz/gal+1/6 Tsp NIS/gal+Sodium Polyphosphate 4 oz/gal
M. 50% Hydrogen Peroxide 6 oz/gal+1/6 Tsp NIS/gal+Sodium Polyphosphate 4 oz/gal+Dicocodimethylammonium chloride 2C75 0.5 oz/gal N. 50% Hydrogen Peroxide 6 oz/gal+1/6 Tsp NIS/gal+EGTA 1 oz/gal
O. 50% Hydrogen Peroxide 6 oz/gal+1/6 Tsp NIS/gal+EGTA 1 oz/gal+Tris 0.5 oz/gal
P. 50% Hydrogen Peroxide 6 oz/gal+1/6 Tsp NIS/gal+Adjuvant 14 oz/gal cocotrimethylammonium chloride 0.5 oz/gal
Q. 50% Hydrogen Peroxide 6 oz/gal+1/6 Tsp NIS/gal+Adjuvant 14 oz/gal+POE 15 beeftallowamine 0.5 oz/gal
R. 50% Hydrogen Peroxide 6 oz/gal+1/6 Tsp NIS/gal+Adjuvant 14 oz/gal+ditallowedimethylammonium chloride 0.5 oz/gal
S. 50% Hydrogen Peroxide 6 oz/gal+1/6 Tsp NIS/gal+Adjuvant 14 oz/gal+tallowtrimethylammonium chloride 0.5 oz/gal
T. 50% Hydrogen Peroxide 6 oz/gal+1/6 Tsp NIS/gal+Adjuvant 54 oz per gallon
U. 50% Hydrogen Peroxide 6 oz/gal+1/6 Tsp NIS/gal+Adjuvant 54 oz/gal+Dicocodimethylammonium chloride 0.5 oz/gal
V. 50% Hydrogen Peroxide 6 oz/gal+1/6 Tsp NIS/gal+Adjuvant 64 oz per gallon
W. 50% Hydrogen Peroxide 6 oz/gal+1/6 Tsp NIS/gal+$CaCl_2$ 2 oz/gal Herbicidal Efficiency Weed White Clover
Damaged A. 5%
B. 69%
C. 75%
D. 73%
E. 78%
F. 83%
G. 88%
H. 72%
I. 61%
J. 53%
K. 81%
L. 59%
M. 84%
N. 74%
O. 79%
P. 80%
Q. 77%
R. 75%
S. 79%
T. 83%
U. 85%
V. 87%
W. 62%

The data show that hydrogen peroxide by itself had very little effectiveness, but the effectiveness was markedly improved by addition of the permeabilizing agents.

Example 4

Effectiveness of Permeabilizers on Cotton Defoliation and Boll Opening

This test was used to evaluate a specific blend of permeabilizers as enhancers for cotton defoliation and boll opening. The tests were large scale field trials conducted comparing the Adjuvant 1 with ethephon against a commercial product Finish® which contains ethephon and cyclanilide. The field tests were conducted in North Carolina (NC), Louisiana (LA), New Mexico (NM) and Georgia (GA).

Adjuvant I (AdjI) was produced by blending 20 pounds citric acid, 77 pounds oxalic acid, and 3 pounds silica. This product was field tested on cotton with several mixes to determine its performance as a Harvest aid chemical evaluated X days after evaluation. Results are shown below.

| Test No. | State | Chem Rate 1 | Chem Rate 2 | Chem Rate 3 | Defol % | Day | Boll Open* |
|---|---|---|---|---|---|---|---|
| 1 | NC | eth 1#/ac | AdjI 1#ac | DEF 6 oz/ac | 98 | 8 | 4 |
| | NC | eth 1#/ac | cyclan 1#/ac | DEF 6 oz/ac | 98 | 8 | 4 |
| 2 | LA | eth 1#/ac | AdjI 1#/ac | — | 96 | 9 | 5 |
| | LA | eth 1#/ac | cyclan 1#/ac | — | 96 | 9 | 4 |
| 3 | NM | eth 1#/ac | AdjI 1#/ac | Thid 5 oz/ac | 98 | 8 | 5 |
| | NM | eth 1#/ac | cyclan 1#/ac | Thid 5 oz/ac | 93 | 8 | 4 |
| 4 | GA | eth 1#/ac | AdjI 1#/ac | — | 96 | 9 | 5 |
| | GA | eth 1#/ac | cyclan 1#/ac | — | 96 | 9 | 4 |

*Boll Opening as subjective rating: 1 = worst; 5 = best
eth = ethephon;
thid = thidazuron;
cyclan = cyclanilide
1#/ac = 1 pound per acre rate;
DEF = tributylphosphorothioate The data show that ethephon with cyclan, a convention adjuvant, was no more effective than ethephon with the permeabilizer, ADJ 1, described herein.

Example 5

Comparison of Oxalic Acid, EDTA and Citric Acid as Adjuvants

Oxalic acid (Adj II), EDTA (Adj III), and citric acid (Adj IV) were used as an adjuvants with harvest aid chemicals and compared to the commercial products ethephon and ethephon plus cyclanilide. The comparison was for defoliation only at 7 days after spraying on cotton. The tests were conducted on test size field plots, at dosages of 1 pound or 0.5 pounds per acre (#/ac).

| Test No. | Chem Rate 1 | Chem Rate 2 | Defol % | Day |
|---|---|---|---|---|
| 1 | eth 1#/ac | AdjII 1#/ac | 98 | 7 |
| 2 | eth 1#/ac | AdjIII .5#/ac | 96 | 7 |
| 3 | eth 1#/ac | AdjIV 1#/ac | 98 | 7 |
| 4 | eth 1#/ac | cyclan 1#/ac | 98 | 7 |
| 5 | eth 1#/ac | — | 72 | 7 |

The data show that ethephon with any of the adjuvants is about as effective as ethephon and cyclan, and significantly more effective than ethephon alone.

Example 6

Effect of Permeabilizers on Speed

This example was used to how various permeabilizers are able to improve the speed in which various active components are able to obtain their desired effects on treated plants. In this example, a combination of oxalic acid and citric acid (Adjuvant 1) was used in combination with the harvest aid chemicals paraquat and diquat for the dessication of potato vines before harvest and compared to the commercial rates paraquat and diquat. The data show that the harvest aid chemicals acted faster even when applied at half the rate compared with the chemicals applied at a full rate in the absence of adjuvant.

| Test No. | Chem Rate 1 | Chem Rate 2 | Defol % | Hour |
|---|---|---|---|---|
| 1 | paraquat 2 qt/ac | None 0 | 98 | 36 |
| 2 | paraquat 1qt/ac | Adj I 1#/ac | 99 | 12 |
| 3 | diquat 1qt/ac | Adj I 1#/ac | 98 | 7 |
| 4 | diquat 2 qt/ac | None 0 | 96 | 24 |

Example 7

Effectiveness of Paraquat in the Presence and Absence of Permeabilizer

This example was a field test conducted on mixed weeds between rows of vegetables using the herbicide paraquat. The herbicide was mixed in water alone (A), and at half rate of paraquat with a permeabilizer (B). At the half rate with the permeabilizer, the degree of weed control was at least as good as at the full rate with no permeabilizer.

A. Paraquat—2 Qts/ac
B. Paraquat—1 Qts/ac+Adjuvant 1 1 lb/ac
Herbicidal Efficiency
Weed Mixed
A 98%
B 100%

Example 8

Efficiency of 2,4-Dichlorophenoxyacetic Acid Butoxyethyl Ester with and without Added Adjuvant This example evaluated the efficiency of the herbicide 2,4 Diclorophenoxyacetic acid butoxyethyl ester (2,4 D) on wild strawberry with a number of permeabilizers. All chemicals were mixed in a spray tank at the given rate and sprayed on the plants. Efficiency was determined as the degree of damage to the strawberry plants at 24 hours after application.

A. 2,4 D 3 oz/gal
B. 2,4 D 3 oz/gal+EDTA 6 oz/gal
C. 2,4 D 3 oz/gal+Dicocodimethylammonium chloride 1.5 oz/gal
D. 2,4 D 3 oz/gal+Oxalic Acid 4 oz/gal
E. 2,4 D 3 oz/gal+Citric Acid 4 oz/gal+Dicocodimethylammonium chloride 4 oz/gal
F. 2,4 D 3 oz/gal+Adjuvant 5
G. 2,4 D 3 oz/gal+Adjuvant 6
Herbicidal Efficiency
Wild Strawberry—1 day rating
A. 9%
B. 56%
C. 76%
D. 83%
E. 88%
F. 85%
G. 87%

The data show that the herbicide had relatively low efficacy in the absence of adjuvant (9%), but significantly higher efficacy in the presence of adjuvant (56-88%).

Example 9

Evaluation of Contact Insecticides

This test was the evaluation of a contact insecticide on the insect the Eastern Tent caterpillar. The insecticide was mixed into a solution and applied to a disc of filter paper. The caterpillars were allowed to crawl on the disc for a specified period of time, then the number living and dead were counted after 1 day.

Insecticide Efficacy
A. Pyrethrin 0.005% 12% Piperonyl Butoxide 0.05%
B. Pyrethrin 0.005% 75% Piperonyl Butoxide 0.05% Adjuvant 1 1%

The data show that the mixture of pyrethrin and piperonyl butoxide was relatively ineffective at killing the caterpillers, but when even a low concentration of Adjuvant 1 was added, the effectiveness improved greatly.

Example 10

Efficacy of a Biological Ingestion Insecticide

This test evaluated the efficacy of a biological ingestion insecticide on the Eastern Tent caterpillar. The insecticide was mixed into a solution and applied to a leaf. The caterpillars was allowed to eat the leaf, then the number living and dead were counted Insecticide Efficacy
A. Bacillis Thuringensis 25% B. Bacillis Thuringensis+EDTA 0.05%+Cocodimethyl+Dicocodimethylammonium chloride 63%

Example 11

Evaluation of an Ingestion Insecticide

This test involved the evaluation of an ingestion insecticide on the Eastern Tent caterpillar. The insecticide was mixed in a tank at the shown rate and sprayed on the tent, and the evaluation was performed after 1 day following application. As shown below, the addition of adjuvant significantly enhanced the efficacy of the insecticide.

Insecticide Efficacy

| | |
|---|---|
| A. Thiodicarb 0.1% | 32% |
| B. Thiodicarb 0.1% + Adjuvant 6 | 56% |

Example 12

Evaluation of Flow Agents

A mixture of organic acids was evaluated in the presence of various flow agents. The flow agents were mixed with a blend of 4 parts oxalic acid and 1 part citric acid at the rate shown. They were evaluated immediately for dustiness, wetting, and overnight in an oven for stability. They were rated for flowability after 4 months. Polyfil DL had the best overall properties of the ones evaluated.

| Flow Agent | % Dustiness | Wetting | Flow | 4 Months Stability |
|---|---|---|---|---|
| HiSil 233 3% | 1 | 10 | 10 | 10 |
| HiSil 233 0.02% | 2 | 10 | 1 | 10 |
| Zinc Stearate 3% | 7 | 8 | 1 | N/A |
| Talc 3% | 10 | 2 | 7 | 10 |
| Agsorb LVM 2% Clay | 3 | 10 | 4 | 10 |
| None | 0 | 10 | 1 | 10 |
| Polyfil DL 3% Clay | 9 | 10 | 10 | 10 |
| Hydral 710 3% A12O3 | 10 | 10 | 1 | 1 |
| Nuzox 78 3% ZnO | 8 | 10 | 2 | 7 |
| Huber DP-70 1% | 8 | 1 | 8 | 8 |
| Lustra Clay 3% | 8 | 10 | 9 | 10 |
| Polyfil DL 1.5% Clay | 9 | 10 | 7 | 10 |
| Diatomaceous 3% Earth | 5 | 10 | 1 | 10 |

Example 13

Evaluation of a Wood Treatment Formulation

A wood treatment formulation was evaluated by dipping blocks of wood into a solution of the listed ingredients in methanol. Blocks were dried and buried in moist soil for 4 months. After the 4 months the blocks were dried and hardness measured by determining the depth of puncture of a given weight on a pointed depth gauge. The data show that the addition of the adjuvant significantly enhanced the wood protection and the hardness of the wood, shown by increased puncture resistance.

Formula Wet Storage—4 months—Puncture Depth mm

| | |
|---|---|
| Cedar Oil | 4 |
| Sodium Tetraborate | |
| Cedar Oil | 1.5 |
| Sodium Tetraborate EDTA | |
| Dicocodimethylammonium chloride 2C | 75 |

Example 14

Effectiveness of Herbicide on Trumpet Vine

This test was used to determine the effectiveness of acifluorifen herbicide on the weed Trumpet vine. The herbicide was mixed with water in a spray tank at the listed rate treatment (A) or with a permeabilizer (B) and the degree of control of the grass was evaluated. The herbicide in the absence of permeabilizer had an effectiveness of only 11% and only slightly damaged the vine leaves. In contrast, the combination of herbicide and adjuvant had an effectiveness of 74%, with major damage to leaves and stem. The ratings were made at 2 days. A week later vines treated with treatment A had nearly recovered while vines treated with treatment B were nearly dead.

A. Acifluorfen—2 oz/gal
B. Acifluorfen—2 oz/gal+Adjuvant 1 80 g/gal
Herbicidal Efficiency
Weed Trumpet Vine
A 11%
B 74%

Example 15

Evaluation of Fungicide for Control of Black Spot on Roses

This example evaluated the effectiveness of the fungicide thiophanate methyl for the control of black spot on roses. The fungicide was mixed with water in a spray tank at the listed rate treatment (A), or with a permeabilizer (B) and the degree of control of the blackspot was evaluated. The ratings were made after one week on the percent leaves infected with blackspot. The data show that the fungicide was only slightly effective in the absence of permeabilizer (20%), but extremely effective (68%) in the presence of the permeabilizer.

A. Thiophanate Methyl—1 oz/gal
B. Thiophanate Methyl—1 oz/gal+Adjuvant 1 80 g/gal
Fungicidal Efficiency % Control
Black Spot Roses A 20%
B 68%

Example 16

Effectiveness of a Bactericide on Bacterial Leaf Spot (*Xanthomonas campestris*) on Tomatoes This example evaluated the effectiveness of the bactericide copper hydroxide for the control of bacterial leaf spot on tomatoes. The tomato plants were innoculated with the bacteria. The bactericide was mixed with water in a spray tank at the listed rate treatment (A), or with a permeabilizer (B) and the degree of control of the leaf spot was evaluated. The ratings were made after two weeks on the percent leaves infected.

| Treatment | Percent Leaves Infected |
|---|---|
| Copper 2#/acre | 63% |
| Copper 1#/ac + Adjuvant 6 (300:1 dilution) | 46% |

The data show that the presence of the adjuvant enhanced the effectiveness of the bactericide. Only about one third of the leaves treated with bactericide alone were uninfected, in comparison to more than half of the leaves treated with the combination of bactericide and adjuvant.

Example 17

Evaluation of Fungicide in the Treatment of Early Blight (*Alternaria solani*)

This example evaluated the effectiveness of the fungicide chlorothalonil for the control of Early Blight on tomatoes.—The fungicide was mixed with water in a spray tank at the listed rate treatment (A), or with a permeabilizer (B) and the degree of control of the Early Blight was evaluated. The tomato plants were innoculated with the fungi. The ratings were made after one week on the percent leaves infected with *Alternaria* and also the number with bad damage—necrosis.

| Leaflets | Infected Leaves | Infected Leaflets | Leaflets with >50% Necrosis |
|---|---|---|---|
| Chlorothalonil 2.5 pt/ac | 42% | 60% | 42% |
| Chlorothalonil 1.25 pt/ac + Adjuvant 6 (300:1 dilution) | 14% | 20% | 14% |

The data show that even when half the amount of fungicide was used, there was a significant decrease in the percentage of infected leaflets, infected leaves, and leaflets with less than 50% necrosis.

Example 18

Effectiveness of Bactericide Streptomycin at Controlling Fireblight

This example evaluated the effectiveness of the bactericide streptomycin for the control of fireblight on Southern Crepe Myrtle. The bactericide was mixed with water in a spray tank at the listed rate treatment (A), or with a permeabilizer (B). The infected plants were treated with the bactericide by spraying until wet and the degree of control of the fireblight was evaluated. The ratings were made after two days on the rate required for control.

Level Required for Control

| | |
|---|---|
| A. Streptomycin | 60 ppm |
| B. Streptomycin + Adjuvant 6 (500:1 dilution) | 20 ppm |

The data show that the presence of adjuvant significantly lowered (by a factor of 2 thirds) the amount of bactericide needed to control fireblight.

Example 19

Cotton Defoliation

This example shows the degree of defoliation of a number of commercial tank mixes after 12 days following application to cotton plants. The mixes were prepared at the rate shown and sprayed on mature cotton plants. Higher defoliation levels are preferred for harvesting.

| Rates Per Acre | 12 Day Defoliation % |
|---|---|
| Dimethepin 8 oz + tributylphosphorothioate 8 oz. | 88% |
| Dimethepin 8 oz. + ethephon 21.33 oz | 82% |
| (Dimethepin + thidiazuron) 12 oz | 80% |
| Monocarbamide 64 oz + carfentrazone-ethyl 0.67 oz | 87% |
| Monocarbamide 64 oz + tributylphosphorothioate 6 oz | 86% |
| Monocarbamide 64 oz + carfentrazone-ethyl 0.67 oz + thidiazuron 1.6 oz | 85% |
| Tributylphosphorothioate 8 oz + ethephone 32 oz + thidiazuron 1.6 oz | 92% |
| Carfentrazone 0.67 oz + ethephon 32 oz + thidiazuron 1.6 oz | 89% |
| Carfentrazone 0.67 oz + ethephone 21.33 oz | 85% |
| Carfentrazone 0.67 oz + (ethephon + cyclanilide) 21.33 oz + thidiazuron 1.6 oz | 90% |
| Carfentrazone 0.67 oz + (ethephon + cyclanilide) 21.33 oz | 91% |
| (Ethephon + cyclanilide) 21.33 oz + thidiazuron 1.6 oz + tributylphosphorothioate 4 oz | 92% |
| (Ethephon + cyclanilide) 21.33 oz + (thidiazuron + diuron) 4 oz | 92% |
| Ethephon 16 oz + Adjuvant 1 16 oz + (thidiazuron + diuron) 4 oz | 91% |

Excellent results—91% defoliation—were obtained using ethephon and adjuvant 1, in combination with thidiazuron and diuron

Example 20

Cotton Desiccation

This example shows the degree of desiccation of a number of commercial tank mixes after 12 days. The mixes were prepared at the rate shown and sprayed on mature cotton plants. A lower the degree of desiccation is preferred to increase the value of the cotton at the gin.

| Rates Per Acre | 12 Day Desiccation % |
|---|---|
| Dimethepin 8 oz + tributylphosphorothioate 8 oz | 2% |
| Dimethepin 8 oz + ethephon 21.33 oz | 0% |
| (Dimethepin + thidiazuron) 12 oz | 2% |
| Monocarbamide 64 oz + carfentrazone-ethyl 0.67 oz | 0% |
| Monocarbamide 64 oz + tributylphosphorothioate 6 oz | 1% |
| Monocarbamide 64 oz + carfentrazone-ethyl 0.67 oz + thidiazuron 1.6 oz | 4% |
| Tributylphosphorothioate 8 oz + ethephon 32 oz + thidiazuron 1.6 oz | 1% |
| Carfentrazone 0.67 oz + ethephon 32 oz + thidiazuron 1.6 oz | 5% |
| Carfentrazone 0.67 oz + ethephon 21.33 oz | 5% |
| Carfentrazone 0.67 + (ethephon + cyclanilide) 21.33 oz + thidiazuron 1.6 oz | 5% |
| Carfentrazone 0.67 oz + (ethephon + cyclanilide) 21.33 oz | 1% |
| (Ethephon + cyclanilide) 21.33 oz + thidiazuron 1.6 oz. + tributylphosphorothioate 4 oz | 1% |
| (Ethephon + cyclanilide) 21.33 oz + (thidiazuron + diuron) 4 oz | 0% |
| Ethephon 16 oz + Adjuvant 1 16 oz + (thidiazuron + diuron) 4 oz | 0% |

Excellent results—0% desiccation BB—were obtained using ethephon and adjuvant 1, in combination with thidiazuron and diuron.

Example 21

Cotton Regrowth Control

This example shows the effectiveness of a number of compounds for regrowth control.

| Rates Per Acre | 14 Day Regrowth % |
| --- | --- |
| Dimethepin 8 oz + tributylphosphorothioate 8 oz | 4% |
| Dimethepin 8 oz + ethephon 21.33 oz | 4% |
| (Dimethepin + thidiazuron) 12 oz | 2% |
| Monocarbamide 64 oz + carfentrazone-ethyl 0.67 oz | 1% |
| Monocarbamide 64 oz + tributylphosphorothioate 6 oz | 3% |
| Monocarbamide 64 oz + carfentrazone-ethyl 0.67 oz + thidiazuron 1.6 oz | 0% |
| Tributylphosphorothioate 8 oz + ethephon 32 oz + thidiazuron 1.6 oz | 0.4% |
| Carfentrazone 0.67 oz + ethephon 32 oz + thidiazuron 1.6 oz | 0% |
| Carfentrazone 0.67 oz + ethephon 21.33 oz | 1% |
| Carfentrazone 0.67 oz + (ethephon + cyclanilide) 21.33 oz + thidiazuron 1.6 oz | 1% |
| Carfentrazone 0.67 oz + (ethephon + cyclanilide) 21.33 oz | 1% |
| (Ethephon + cyclanilide) 21.33 oz + thidiazuron 1.6 oz + tributylphosphorothioate 4 oz | 1% |
| (Ethephon + cyclanilide) 21.33 oz + (thidiazuron + diuron) 4 oz | 0.4% |
| Ethephon 16 oz + Adjuvant 1 16 oz + (thidiazuron + diuron) 4 oz | 0.4% |

The data show excellent results—0.4% regrowth for DDD—with a combination of ethephon, adjuvant 1, thidiazuron and diuron.

References

In this application, the following publications are referenced. The disclosures of these publications in their entireties are hereby incorporated into this application by reference in order to more fully describe the state of the art to which this invention pertains.

1. G. W. Cathey, Chapter 14 Physiology of Cotton Defoliation in Cotton Production, Cotton Physiology, The Cotton Foundation, p. 143-154.

2. P. W. Morgan and J. I. Durham, Plants, 110, 91-93 (1973).

3. K. H. Hasenstein and M. L. Evans, Plant Physiol., (1986) 81, 439-443.

4. P. M. Tang, R. K. dela Fuenta, Plant Physiol, (1986) 81, 651-655.

5. A. C. Leopold, Chapter 4, Modification of Growth Regulatory Action with Inorganic Solutes, Plant Growth Reaulators. ACS Advances in Chemistry Series, Number 159, 1977, p. 33-41.

The invention has been clearly described in detail, with particular reference to certain preferred embodiments, in order to enable the reader to practice the invention without undue experimentation. Theories have been offered to better enable the reader to understand the invention, but such theories do not limit the scope of the invention. In addition, a person having ordinary skill in the art will readily recognize that many of the previous components and parameters may be varied or modified to a reasonable extent without departing from the scope and spirit of the invention. Accordingly, the invention is defined by the following claims, and reasonable extensions and equivalents thereof.

What is claimed is:

1. A method of increasing the speed or degree of cotton boll opening comprising the steps of
providing a composition comprising an adjuvant and at least one plant growth regulating compound ethephon and tributylphosphorthioate and combination thereof, wherein the adjuvant comprises at least one permeabilizing agent and at least one flow agent selected from the group consisting of silica, clay, kaolin, talc, and diatomaceous earth and combination thereof in an amount between 0.1% and 10%, wherein the at least one permeabilizing agent is a combination of citric acid and oxalic acid, wherein the citric acid is present in an amount of between 1% w/w and about 20% w/w of the adjuvant, and wherein the oxalic acid is present in an amount of between about 77% w/w and 98% w/w of the adjuvant; and
applying the composition to at least one plant surface in an amount sufficient to increase the speed or degree of opening of at least one cotton boll compared to the speed or degree of opening upon application of the at least one plant growth regulating compound alone.

2. The method of claim 1, wherein the at least one plant surface is at least one part of a cotton plant that is above the ground, prior to cotton harvest.

3. The method of claim 2, wherein the at least one part of a cotton plant that is above the ground, prior to cotton harvest is chosen from a leaf, stem, boll or a combination thereof.

4. The method of claim 1, wherein the citric acid is present in an amount of 20% w/w of the adjuvant.

5. The method of claim 1, wherein the oxalic acid is present in an amount of 77% w/w of the adjuvant.

6. The method of claim 1, wherein the at least one flow agent is silica present in an amount of between 0.1% w/w and 5% w/w of the adjuvant.

7. The method of claim 6, wherein the silica is present in an amount of 3% w/w of the adjuvant.

8. The method of claim 1, wherein the at least one plant growth regulating compound futher comprise thidazuron, paraquat, diquat, endothall, chlorates, cacodylic acid and its sodium salt, monosodium methyl arsenate(MSMA), diuron, dimethipin, monocarbamide, carfentrazone, cyclanalide, thidiazuron or a combination thereof.

9. The method of claim 1, wherein the at least one plant growth regulating compound is ethephon.

10. The method of claim 1, wherein the composition is applied at a rate of from 0.25 to 2.5 pounds per acre.

* * * * *